United States Patent [19]

Schallner et al.

[11] Patent Number: 4,806,144
[45] Date of Patent: Feb. 21, 1989

[54] 5-SULPHONAMIDO-1-ARYL-PYRAZOLES

[75] Inventors: Otto Schallner, Monheim; Reinhold Gehring; Jörg Stetter, both of Wuppertal; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 817,181

[22] Filed: Jan. 8, 1986

[30] Foreign Application Priority Data

Feb. 2, 1985 [DE] Fed. Rep. of Germany ....... 3503609

[51] Int. Cl.$^4$ .................. A01N 43/56; C07D 231/1H
[52] U.S. Cl. ........................................ 71/92; 548/375; 548/376
[58] Field of Search ..................... 71/92; 548/375, 376

[56] References Cited

U.S. PATENT DOCUMENTS

| | | | |
|---|---|---|---|
| 3,398,158 | 8/1968 | Fusen et al. ......................... | 548/375 |
| 4,459,150 | 7/1984 | Hatton et al. . | |
| 4,496,390 | 1/1985 | Hatton et al. . | |
| 4,614,530 | 9/1986 | Schillner et al. ...................... | 71/92 |
| 4,666,507 | 5/1987 | Yanagi et al. ......................... | 71/92 |

FOREIGN PATENT DOCUMENTS 1467832 11/1968 Fed. Rep. of Germany .
1462155 11/1966 France .
2008400 1/1970 France .
865341 4/1961 United Kingdom .

OTHER PUBLICATIONS

*J. Heterocyclic Chem.*, 7, pp. 345–349 (1970), Michael D. Coburn, "Picrylamino-substituted Heterocycles. IV. Pyrazoles (1,2)".
*J. Org. Chem.*, vol. 36, No. 20, 1971, pp. 2972–2974, Yusuf Ahmad and Peter A. S. Smith, "Pyrazolotriazines from Condensation of Nitro with Amino Groups".
*J. Heterocyclic Chem.*, 19, page 1267, (1982), Gunter Ege and Hermann Franz, "Aminopyrazoles. IV (1). Pyrazol-3- and 5-amines from 2,3-Dihaloalkanenitriles or 3-Chloroacrylonitriles and Hydrazines".
*J. Heterocyclic Chem.*, 19, page 1265, (1982), Gunter Ege and Hermann Franz, "Aminopyrazoles III(1) Novel 'One-Flask' Preparation of 1-Phenylpyrazol-3-amine".
*Heterocyclic Compounds*, vol. 62, 1965, Col. 13157, "Derivatives of 1,4-thiazane 1,1-dioxide".
*Journal f. prakt. Chemie.*, Band 321, Heft 1, 1979, S. 93–101, Helmut Dorn, Rudiger Ozegowski, "Die Reaktion von α, β-Dihalogen-propionitrilen mit monosubstituierten Hydrazinen-einfache Synthese 1-substituierter 3-bzw . . . ".
Houbel-Weyl, *"Methoden der organischen Chemie"*, (M'Methods of Organic Chemistry'), vol. X,2, Thieme Verlag Stuttgart, 1967).

*Primary Examiner*—Catherine L. Mills
*Attorney, Agent, or Firm*—Sprung Horn Kramer & Woods

[57] ABSTRACT

A 5-sulphonamido-1-aryl-pyrazole of the formula (I)

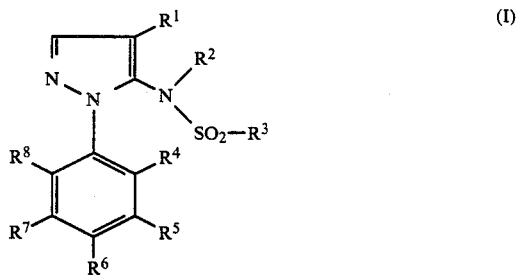

in which $R^1$ represents hydrogen, nitro, nitroso or halogen, $R^2$ represents hydrogen, alkyl or a radical $R^3$—$SO_2$—, or an inorganic or organic cation bonded in the form of a salt, $R^3$ represents alkyl, alkenyl, cycloalkyl, halogeno-alkyl, hydroxyalkyl, alkoxyalkyl or unsubstituted or substituted aryl, $R^4$ and $R^6$ independently of one another represent cyano, nitro, halogen, alkyl, alkoxy, alkoxycarbonyl, halogenoalkyl, halogenoalkoxy or a radical —(O)-$_n$—$R^9$ and $R^5$, $R^7$ and $R^8$ independently of one another and of $R^4$ and $R^6$ represent the same radicals as $R^4$ and $R^6$, and additionally represent hydrogen, wherein $R^9$ represents alkyl, halogenoalkyl, amino, alkyl-amino or dialkylamino and n represents the number 0, 1 or 2.

Such 5-sulphonamido-1-aryl-pyrazole being useful as a herbicide.

15 Claims, No Drawings

5-SULPHONAMIDO-1-ARYL-PYRAZOLES

BACKGROUND OF THE INVENTION

The invention relates to new 5-sulphonamido-1-aryl-pyrazoles, several processes for their preparation and their use as herbicides.

It is already known that certain 1-aryl-pyrazoles, such as, for example, 4-cyano-5-propionamido-1-(2,3,4-trichlorophenyl)-pyrazole, have herbicidal properties, and in particular also selectively herbicidal properties (compare, for example, DE-OS (German Published Specification) No. 3,226,513).

The herbicidal activity of these already known 1-aryl-pyrazoles against harmful plants is, however, like their tolerance towards important crop plants, not always completely satisfactory in all fields of use.

SUMMARY OF THE INVENTION

New 5-sulphonamido-1-aryl-pyrazoles according to the present invention are of the general formula (I)

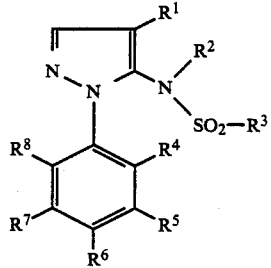

in which
$R^1$ represents hydrogen, nitro, nitroso or halogen,
$R^2$ represents hydrogen, alkyl or a radical $R^3$—$SO_2$—, or an inorganic or organic cation bonded in the form of a salt,
$R^3$ represents alkyl, alkenyl, cycloalkyl, halogenoalkyl, hydroxyalkyl, alkoxyalkyl or in each case unsubstituted or substituted aryl,
$R^4$ and $R^6$ independently of one another represent cyano, nitro, halogen, alkyl, alkoxy, alkoxycarbonyl, halogenoalkyl, halogenoalkoxy or a radical —$S(O)_n$—$R^9$ and
$R^5$, $R^7$ and $R^8$ independently of one another and of $R^4$ and $R^6$ represent the same radicals as $R^4$ and $R^6$, and additionally represent hydrogen,
wherein
$R^9$ represents alkyl, halogenoalkyl, amino, alkylamino or dialkylamino and
n represents the number 0, 1 or 2.

It has furthermore been found that the new 5-sulphonamido-1-aryl-pyrazoles of the general formula (I)

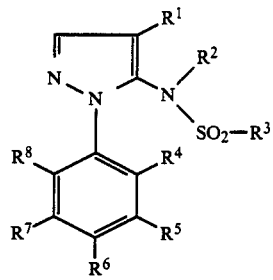

in which
$R^1$ represents hydrogen, nitro, nitroso or halogen,
$R^2$ represents hydrogen, alkyl or a radical $R^3$—$SO_2$—, or an inorganic or organic cation bonded in the form of a salt,
$R^3$ represents alkyl, alkenyl, cycloalkyl, halogenoalkyl, hydroxylkyl, alkoxyalkyl or in each case unsubstituted or substituted aryl,
$R^4$ and $R^6$ independently of one another represent cyano, nitro, halogen, alkyl, alkoxy, alkoxycarbonyl, halogenoalkyl, halogenoalkoxy or a radical —$S(O)_n$—$R^9$ and
$R^5$, $R^7$ and $R^8$ independently of one another and of $R^4$ and $R^6$ represent the same radicals as $R^4$ and $R^6$, and additionally represent hydrogen,
wherein
$R^9$ represents alkyl, halogenoalkyl, amino, alkylamino or dialkylamino and
n represents the number 0, 1 or 2,
are obtained by a process in which
(a) 5-aminopyrazoles of the formula (II)

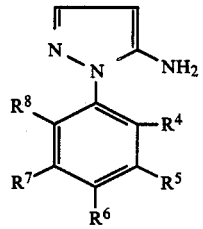

in which $R^4$, $R^5$, $R^6$, $R^7$ and $R^8$ have the abovementioned meaning, are reacted with sulphonyl chlorides of the formula (III)

in which $R^3$ has the abovementioned meaning, if appropriate in the presence of a diluent and if appropriate in the presence of an acid-binding agent, or in which (b) the bisulphonylamines obtainable according to the process (a), of the formula (Ia)

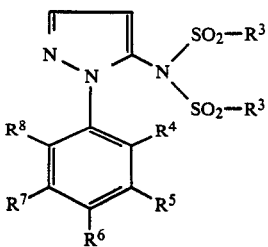

in which $R^3$, $R^4$, $R^5$, $R^6$, $R^7$ and $R^8$ have the abovementioned meaning, are split with bases, if appropriate in the presence of a diluent, or in which (c) the 5-sulphonamido-pyrazoles obtainable according to process (a) or (b), of the formula (Ib)

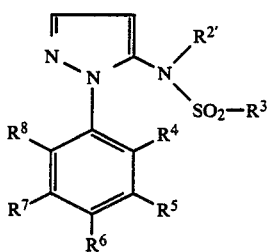

in which $R^{2'}$ represents hydrogen or a radical $R^3$—$SO_2$— and $R^3$, $R^4$, $R^5$, $R^6$, $R^7$ and $R^8$ have the abovementioned meaning, are subjected to substitution in the 4-position with electrophilic agents of the formula (IV)

$$R^{1'}\text{—E} \qquad (IV)$$

in which $R^{1'}$ represents halogen, nitroso or nitro and

E represents an electron-withdrawing leaving grouping, if appropriate in the presence of a diluent and if appropriate in the presence of a catalyst or reaction auxiliary, or in which (d) the 5-sulphonamido-pyrazoles obtainable according to process (a), (b) or (c), of the formula (Ic)

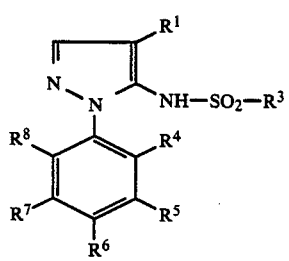

in which $R^1$, $R^3$, $R^4$, $R^5$, $R^6$, $R^7$ and $R^8$ have the abovementioned meaning, either (i) are alkylated on the nitrogen atom of the sulphonamido group with alkylating agents of the formula (V)

$$R^{2''}\text{—E'} \qquad (V)$$

in which $R^{2''}$ represents alkyl and

E' represents an electron-withdrawing leaving group, if appropriate in the presence of a diluent and if appropriate in the presence of an acid-binding agent or catalyst, or (ii) forms a salt on the nitrogen of the sulphonamido group with compounds of the formula (VI)

$$M^{\oplus}G^{\ominus} \qquad (VI)$$

in which $M^{\oplus}$ represents one equivalent of an inorganic or organic cation and $G^{\ominus}$ represents one equivalent of a suitable counterion, or with primary, secondary or tertiary amines, if appropriate in the presence of a diluent.

Finally, it has been found that the new 5-sulphonamido-1-aryl-pyrazoles of the general formula (I) have herbicidal properties, and in particular also selectively herbicidal properties.

DETAILED DESCRIPTION OF THE INVENTION

Surprisingly, the 5-sulphonamido-1-aryl-pyrazoles of the general formula (I), besides having a clearly improved generally herbicidal activity towards harmful plants, exhibit a considerably improved tolerance towards important crop plants in comparison with the 1-aryl-pyrazoles known from the prior art, such as, for example, 4-cyano-5-propionylamino-1-(2,3,4-trichlorophenyl)-pyrazole, which is a closely related compound chemically and from the point of view of its action.

Formula (I) provides a general definition of the 5-sulphonamido-1-aryl-pyrazoles according to the invention. Preferred compounds of the formula (I) are those in which:

$R^1$ represents hydrogen, nitro, nitroso or halogen, $R^2$ represents hydrogen, straight-chain or branched alkyl with 1 to 8 carbon atoms, a radical $R^3$—$SO_2$—, one equivalent of an alkali metal, alkaline earth metal or transition metal cation or an unsubstituted or substituted ammonium ion, $R^3$ represents in each case straight-chain or branched alkyl, alkenyl, halogenoalkyl, alkoxyalkyl or hydroxyalkyl with in each case up to 4 carbon atoms and for the halogenoalkyl up to 9 identical or different halogen atoms, or represents cycloalkyl with 3 to 7 carbon atoms, or represents benzyl or phenyl, each of which is unsubstituted or monosubstituted or polysubstituted by identical or different substituents from the group comprising halogen, cyano, nitro and in each case lower alkyl, alkoxy, alkylthio and halogenoalkyl, $R^4$ and $R^6$ independently of one another represent cyano, halogen or in each case straight-chain or branched alkyl, alkoxy or alkoxycarbonyl with in each case up to 4 carbon atoms, or in each case straight-chain or branched halogenoalkyl or halogenoalkoxy, with in each case up to 4 carbon atoms and up to 9 identical or different halogen atoms, or a radical —$S(O)_n$—$R^9$ and $R^5$, $R^7$ and $R^8$ independently of one another and independently of $R^4$ and $R^6$ represent the same radicals as $R^4$ and $R^6$, and additionally represent hydrogen, wherein $R^9$ represents amino or in each case straight-chain or branched alkyl, alkylamino, dialkylamino or halogenoalkyl, with in each case up to 4 carbon atoms in the individual alkyl parts and, in the case of the halogenoalkyl, with up to 9 identical or different halogen atoms, and n represents the number 0, 1 or 2.

Particularly preferred compounds of the formula (I) are those in which $R^1$ represents hydrogen, nitro, nitroso, fluorine, chlorine, bromine or iodine, $R^2$ represents hydrogen, methyl, ethyl, n- or i-propyl, n-, i-, s- or t-butyl, a radical $R^3$—$SO_2$—, one equivalent of a sodium, potassium, magnesium, calcium, barium, copper, zinc, manganese, tin, iron, cobalt or nickel ion, or an ammonium ion which is unsubstituted or mono-, di- or tri-substituted by identical or different substituents from the group comprising methyl, ethyl, n- or i-propyl, n-, i-, s- and t-butyl or phenyl, $R^3$ represents methyl, ethyl, n- or i-propyl, n-, i-, s- or t-butyl, allyl, butenyl, methoxymethyl, methoxyethyl, hydroxymethyl, hydroxyethyl, chloromethyl, dichloromethyl, trifluoromethyl, cyclopropyl, cyclopentyl or cyclohexyl, or benzyl or phenyl, each of which is unsubstituted or mono-, di- or tri-substituted by identical or different substituents, possible substituents being: fluorine, chlorine, bromine, cyano, nitro, methyl, ethyl, methoxy, methylthio or trifluoromethyl, $R^4$ and $R^6$ independently of one another represent cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical —$S(O)_n$—$R^9$ and $R^5$, $R^7$ and $R^8$ independently of one another and independently of $R^4$ and $R^6$ represent the same radicals as $R^4$ and $R^6$, and additionally represent hydrogen, wherein $R^9$ represents amino, methylamino, ethylamino, dimethylamino, diethylamino, fluorodichloromethyl, difluoromethyl, tetrafluoroethyl, trifluorochloroethyl, trifluoromethyl, methyl or ethyl and n represents the number 0, 1 or 2.

The 5-sulphonamido-1-aryl-pyrazoles of the general formula (I) listed in the following table may be mentioned specifically, in addition to the compounds mentioned in the preparation examples:

TABLE 1

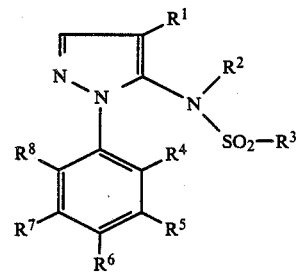

(I)

| $R^1$ | $R^2$ | $R^3$ | $R^4$ | $R^5$ | $R^6$ | $R^7$ | $R^8$ |
|---|---|---|---|---|---|---|---|
| H | H | $CH_3$ | Cl | H | Cl | H | Cl |
| H | H | $CH_3$—⟨phenyl⟩— | Cl | H | Cl | H | Cl |
| H | H | $CH_3$—⟨phenyl⟩— | Cl | H | $CF_3$ | H | Cl |
| H | H | $CH_3$ | Cl | Cl | Cl | H | H |
| H | H | $CH_3$ | Cl | H | $CF_3$ | H | Br |
| H | $CH_3$ | $CH_3$ | Cl | Cl | $CF_3$ | H | Cl |
| H | H | $CH_3$ | Cl | F | $CF_3$ | Cl | Cl |
| H | H | $CH_3$ | Cl | F | $CF_3$ | F | F |
| H | H | $CH_3$ | F | F | $CF_3$ | F | F |
| H | H | $CH_3$ | Cl | F | Cl | F | Cl |
| H | H | $C_2H_5$ | Cl | H | Br | H | Cl |
| H | H | $CH_3$ | F | F | F | F | F |
| H | $C_2H_5$ | $CH_2Cl$ | Cl | H | $CF_3$ | H | H |
| H | $(CH_2)_2OH$ | $CF_3$ | Cl | Cl | Cl | H | H |
| H | H | $CH_3$ | Cl | H | $OCF_3$ | H | Cl |
| H | H | $C_4H_9$ | Cl | H | $SCF_3$ | H | Cl |
| H | $CH_3$ | $CH_3$ | Cl | Cl | $OCF_3$ | H | Cl |
| H | H | $(CH_2)_2Cl$ | Cl | Cl | $SCF_3$ | H | Cl |
| H | H | $CF_3$ | Cl | Cl | Cl | H | Cl |
| H | H | $CF_3$ | Cl | H | Cl | H | Cl |
| H | $CH(CH_3)_2$ | $CH_3$ | Br | H | Br | H | Br |

TABLE 1-continued

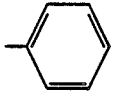

(I)

| R¹ | R² | R³ | R⁴ | R⁵ | R⁶ | R⁷ | R⁸ |
|---|---|---|---|---|---|---|---|
| H | H | C₄H₉ | Br | H | CH₃ | H | H |
| H | H | C₄H₉ | Cl | H | OCF₂CHF₂ | H | H |
| H | H | CH₃ | Cl | H | SO₂CCl₂F | H | Cl |
| H | H | CH₃ | Cl | H | SO₂CClF₂ | H | Cl |
| H | CH₃ | CH₂Cl | Br | H | SCF₃ | H | Br |
| H | H | C₄H₉ | Br | H | SCF₃ | H | H |
| H | H | CH₃ | CF₃ | F | Cl | H | Cl |
| H | CH₃ | CH₃ | CF₃ | H | Cl | H | H |
| H | H | C₄H₉ | CF₃ | H | Br | H | H |
| H | H | CH₃ | Cl | F | CN | F | Cl |
| H | H | CH₃ | F | F | CN | F | F |
| H | H | CH₃ | F | Cl | F | Cl | F |
| H | H | 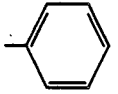 | Cl | Cl | CF₃ | H | Cl |
| H | CH₃ | 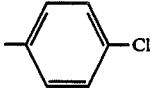 | Cl | H | OCF₃ | H | H |
| H | CH₃ |  | Cl | H | CF₃ | H | Cl |
| H | H | (4-NO₂-phenyl) | Cl | H | CF₃ | H | Cl |
| H | CH₃ | CH₂Cl | Cl | H | CF₃ | H | H |
| H | C₃H₇ | CH₃ | Cl | Cl | CF₃ | H | Cl |
| H | (CH₂)₂OH | C₄H₉ | Cl | H | SO₂CF₃ | H | Cl |
| H | H | CH₃ | Cl | H | SO₂CF₃ | H | H |
| H | H | CH₃ | Cl | H | SOCF₃ | H | H |
| H | H | CH₃ | Cl | Cl | Cl | H | Cl |
| H | H | CF₃ | Cl | H | OCF₃ | H | Cl |
| H | CH₃ | CF₃ | Cl | Cl | Cl | H | H |
| H | H | C₄F₉ | Cl | Cl | CF₃ | H | Cl |
| H | CH₃ | C₄F₉ | Cl | H | SCF₃ | H | Cl |
| H | H | CH₃ | CF₃ | H | CF₃ | H | H |
| H | H | CH₃ | Cl | H | NO₂ | H | Cl |
| H | H | CH₃ | NO₂ | H | NO₂ | H | H |
| H | H | CH₃ | Cl | H | CH₃ | H | Cl |
| H | H | CF₃ | Cl | H | CH(CH₃)₂ | H | Cl |
| H | H | CH₂Cl | Cl | H | C(CH₃)₃ | H | Cl |
| H | H | CH₃ | Br | H | OCF₃ | H | Cl |
| NO | H | CH₃ | Cl | H | CF₃ | H | Br |
| NO | CH₃ | CH₃ | Cl | Cl | CF₃ | H | Cl |
| NO | H | CH₃ | Cl | F | CF₃ | Cl | Cl |
| NO | H | CH₃ | Cl | F | CF₃ | F | F |
| NO | H | CH₃ | F | F | CF₃ | F | F |
| NO | H | CH₃ | Cl | F | Cl | F | Cl |
| NO | H | C₂H₅ | Cl | H | Br | H | Cl |
| NO | H | CH₃ | F | F | F | F | F |
| NO | C₂H₅ | CH₂Cl | Cl | H | CF₃ | H | H |
| NO | (CH₂)₂OH | CF₃ | Cl | Cl | Cl | H | H |
| NO | H | CH₃ | Cl | H | OCF₃ | H | Cl |
| NO | H | C₄H₉ | Cl | H | SCF₃ | H | Cl |
| NO | CH₃ | CH₃ | Cl | Cl | OCF₃ | H | Cl |

TABLE 1-continued (I) Structure: pyrazole with R¹ at 4-position, N-R² and SO₂-R³ substituents at 5-position amino group, and N-phenyl at 1-position with R⁴, R⁵, R⁶, R⁷, R⁸ on the phenyl ring.

| R¹ | R² | R³ | R⁴ | R⁵ | R⁶ | R⁷ | R⁸ |
|---|---|---|---|---|---|---|---|
| NO | H | (CH$_2$)$_2$Cl | Cl | Cl | SCF$_3$ | H | Cl |
| NO | H | CF$_3$ | Cl | Cl | Cl | H | Cl |
| NO | H | CF$_3$ | Cl | H | Cl | H | Cl |
| NO | CH(CH$_3$)$_2$ | CH$_3$ | Br | H | Br | H | Br |
| NO | H | C$_4$F$_9$ | Br | H | CH$_3$ | H | H |
| NO | H | C$_4$H$_9$ | Cl | H | OCF$_2$CHF$_2$ | H | H |
| NO | H | CH$_3$ | Cl | H | SO$_2$CCl$_2$F | H | Cl |
| NO | H | CH$_3$ | Cl | H | SO$_2$CClF$_2$ | H | Cl |
| NO | CH$_3$ | CH$_2$Cl | Br | H | SCF$_3$ | H | Br |
| NO | H | C$_4$H$_9$ | Br | H | SCF$_3$ | H | H |
| NO | H | CH$_3$ | CF$_3$ | F | Cl | H | Cl |
| NO | CH$_3$ | CH$_3$ | CF$_3$ | H | Cl | H | H |
| NO | H | C$_4$H$_9$ | CF$_3$ | H | Br | H | H |
| NO | H | CH$_3$ | Cl | F | CN | F | Cl |
| NO | H | CH$_3$ | F | F | CN | F | F |
| NO | H | CH$_3$ | F | Cl | F | Cl | F |
| NO | H | phenyl | Cl | Cl | CF$_3$ | H | Cl |
| NO | CH$_3$ | phenyl | Cl | H | OCF$_3$ | H | H |
| NO | CH$_3$ | 4-Cl-phenyl | Cl | H | CF$_3$ | H | Cl |
| NO | H | 4-NO$_2$-phenyl | Cl | H | CF$_3$ | H | Cl |
| NO | CH$_3$ | CH$_2$Cl | Cl | H | CF$_3$ | H | H |
| NO | C$_3$H$_7$ | CH$_3$ | Cl | Cl | CF$_3$ | H | Cl |
| NO | (CH$_2$)$_2$OH | C$_4$H$_9$ | Cl | H | SO$_2$CF$_3$ | H | Cl |
| NO | H | CH$_3$ | Cl | H | SO$_2$CF$_3$ | H | H |
| NO | H | CH$_3$ | Cl | H | SOCF$_3$ | H | H |
| NO | H | CH$_3$ | Cl | Cl | Cl | H | Cl |
| NO | H | CF$_3$ | Cl | H | OCF$_3$ | H | Cl |
| NO | CH$_3$ | CF$_3$ | Cl | Cl | Cl | H | H |
| NO | H | C$_4$F$_9$ | Cl | Cl | CF$_3$ | H | Cl |
| NO | CH$_3$ | C$_4$F$_9$ | Cl | H | SCF$_3$ | H | Cl |
| NO | H | CH$_3$ | CF$_3$ | H | CF$_3$ | H | H |
| NO | H | CH$_3$ | Cl | H | NO$_2$ | H | Cl |
| NO | H | CH$_3$ | NO$_2$ | H | NO$_2$ | H | H |
| NO | H | CH$_3$ | Cl | H | CH$_3$ | H | Cl |
| NO | H | CF$_3$ | Cl | H | CH(CH$_3$)$_2$ | H | Cl |
| NO | H | CH$_2$Cl | Cl | H | C(CH$_3$)$_3$ | H | Cl |
| NO | H | CH$_3$ | Br | H | OCF$_3$ | H | Cl |
| NO$_2$ | H | CH$_3$ | Cl | H | CF$_3$ | H | Br |
| NO$_2$ | CH$_3$ | CH$_3$ | Cl | Cl | CF$_3$ | H | Cl |
| NO$_2$ | H | CH$_3$ | Cl | F | CF$_3$ | Cl | Cl |
| NO$_2$ | H | CH$_3$ | Cl | F | CF$_3$ | F | F |
| NO$_2$ | H | CH$_3$ | F | F | CF$_3$ | F | F |
| NO$_2$ | H | CH$_3$ | Cl | F | Cl | F | Cl |
| NO$_2$ | H | C$_2$H$_5$ | Cl | H | Br | H | Cl |
| NO$_2$ | H | CH$_3$ | F | F | F | F | F |
| NO$_2$ | C$_2$H$_5$ | CH$_2$Cl | Cl | H | CF$_3$ | H | H |

TABLE 1-continued

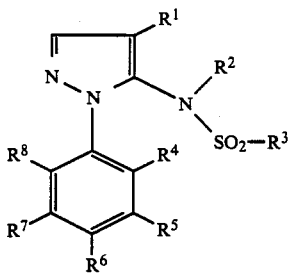

| R¹ | R² | R³ | R⁴ | R⁵ | R⁶ | R⁷ | R⁸ |
|---|---|---|---|---|---|---|---|
| NO₂ | (CH₂)₂OH | CF₃ | Cl | Cl | Cl | H | H |
| NO₂ | H | CH₃ | Cl | H | OCF₃ | H | Cl |
| NO₂ | H | C₄H₉ | Cl | H | SCF₃ | H | Cl |
| NO₂ | CH₃ | CH₃ | Cl | Cl | OCF₃ | H | Cl |
| NO₂ | H | (CH₂)₂Cl | Cl | Cl | SCF₃ | H | Cl |
| NO₂ | H | CF₃ | Cl | Cl | Cl | H | Cl |
| NO₂ | H | CF₃ | Cl | H | Cl | H | Cl |
| NO₂ | CH(CH₃)₂ | CH₃ | Br | H | Br | H | Br |
| NO₂ | H | C₄F₉ | Br | H | CH₃ | H | H |
| NO₂ | H | C₄H₉ | Cl | H | OCF₂CHF₂ | H | H |
| NO₂ | H | CH₃ | Cl | H | SO₂CCl₂F | H | Cl |
| NO₂ | H | CH₃ | Cl | H | SO₂CClF₂ | H | Cl |
| NO₂ | CH₃ | CH₂Cl | Br | H | SCF₃ | H | Br |
| NO₂ | H | C₄H₉ | Br | H | SCF₃ | H | H |
| NO₂ | H | CH₃ | CF₃ | F | Cl | H | Cl |
| NO₂ | CH₃ | CH₃ | CF₃ | H | Cl | H | H |
| NO₂ | H | C₄H₉ | CF₃ | H | Br | H | H |
| NO₂ | H | CH₃ | Cl | F | CN | F | Cl |
| NO₂ | H | CH₃ | F | F | CN | F | F |
| NO₂ | H | CH₃ | F | Cl | F | Cl | F |
| NO₂ | H | ⟨phenyl⟩ | Cl | Cl | CF₃ | H | Cl |
| NO₂ | CH₃ | ⟨phenyl⟩ | Cl | H | OCF₃ | H | H |
| NO₂ | CH₃ | ⟨4-Cl-phenyl⟩ | Cl | H | CF₃ | H | Cl |
| NO₂ | H | ⟨4-NO₂-phenyl⟩ | Cl | H | CF₃ | H | Cl |
| NO₂ | CH₃ | CH₂Cl | Cl | H | CF₃ | H | H |
| NO₂ | C₃H₇ | CH₃ | Cl | Cl | CF₃ | H | Cl |
| NO₂ | (CH₂)₂OH | C₄H₉ | Cl | H | SO₂CF₃ | H | Cl |
| NO₂ | H | CH₃ | Cl | H | SO₂CF₃ | H | H |
| NO₂ | H | CH₃ | Cl | H | SOCF₃ | H | H |
| NO₂ | H | CH₃ | Cl | Cl | Cl | H | Cl |
| NO₂ | H | CF₃ | Cl | H | OCF₃ | H | Cl |
| NO₂ | CH₃ | CF₃ | Cl | Cl | Cl | H | H |
| NO₂ | H | C₄F₉ | Cl | Cl | CF₃ | H | Cl |
| NO₂ | CH₃ | C₄F₉ | Cl | H | SCF₃ | H | Cl |
| NO₂ | H | CH₃ | CF₃ | H | CF₃ | H | H |
| NO₂ | H | CH₃ | Cl | H | NO₂ | H | Cl |
| NO₂ | H | CH₃ | NO₂ | H | NO₂ | H | H |
| NO₂ | H | CH₃ | Cl | H | CH₃ | H | Cl |
| NO₂ | H | CF₃ | Cl | H | CH(CH₃)₂ | H | Cl |
| NO₄ | H | CH₂Cl | Cl | H | C(CH₃)₃ | H | Cl |
| NO₂ | H | CH₃ | Br | H | OCF₃ | H | Cl |
| Cl | H | CH₃ | Cl | H | CF₃ | H | Br |
| Cl | CH₃ | CH₃ | Cl | Cl | CF₃ | H | Cl |
| Cl | H | CH₃ | Cl | F | CF₃ | Cl | Cl |
| Cl | H | CH₃ | Cl | F | CF₃ | F | F |
| Cl | H | CH₃ | F | F | CF₃ | F | F |

TABLE 1-continued

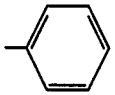

(I)

| R¹ | R² | R³ | R⁴ | R⁵ | R⁶ | R⁷ | R⁸ |
|----|----|----|----|----|----|----|----|
| Cl | H | CH₃ | Cl | F | Cl | F | Cl |
| Cl | H | C₂H₅ | Cl | H | Br | H | Cl |
| Cl | H | CH₃ | F | F | F | F | F |
| Cl | C₂H₅ | CH₂Cl | Cl | H | CF₃ | H | H |
| Cl | (CH₂)₂OH | CF₃ | Cl | Cl | Cl | H | H |
| Cl | H | CH₃ | Cl | H | OCF₃ | H | Cl |
| Cl | H | C₄H₉ | Cl | H | SCF₃ | H | Cl |
| Cl | CH₃ | CH₃ | Cl | Cl | OCF₃ | H | Cl |
| Cl | H | (CH₂)₂Cl | Cl | Cl | SCF₃ | H | Cl |
| Cl | H | CF₃ | Cl | Cl | Cl | H | Cl |
| Cl | H | CF₃ | Cl | H | Cl | H | Cl |
| Cl | CH(CH₃)₂ | CH₃ | Br | H | Br | H | Br |
| Cl | H | C₄F₉ | Br | H | CH₃ | H | H |
| Cl | H | C₄H₉ | Cl | H | OCF₂CHF₂ | H | H |
| Cl | H | CH₃ | Cl | H | SO₂CCl₂F | H | Cl |
| Cl | H | CH₃ | Cl | H | SO₂CClF₂ | H | Cl |
| Cl | CH₃ | CH₂Cl | Br | H | SCF₃ | H | Br |
| Cl | H | C₄H₉ | Br | H | SCF₃ | H | H |
| Cl | H | CH₃ | CF₃ | F | Cl | H | Cl |
| Cl | CH₃ | CH₃ | CF₃ | H | Cl | H | H |
| Cl | H | C₄H₉ | CF₃ | H | Br | H | H |
| Cl | H | CH₃ | Cl | F | CN | F | Cl |
| Cl | H | CH₃ | F | F | CN | F | F |
| Cl | H | CH₃ | F | Cl | F | Cl | F |
| Cl | H | 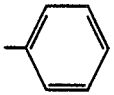 | Cl | Cl | CF₃ | H | Cl |
| Cl | CH₃ | 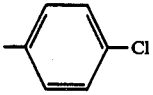 | Cl | H | OCF₃ | H | H |
| Cl | CH₃ | 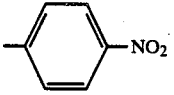 | Cl | H | CF₃ | H | Cl |
| Cl | H |  | Cl | H | CF₃ | H | Cl |
| Cl | CH₃ | CH₂Cl | Cl | H | CF₃ | H | H |
| Cl | C₃H₇ | CH₃ | Cl | Cl | CF₃ | H | Cl |
| Cl | (CH₂)₂OH | C₄H₉ | Cl | H | SO₂CF₃ | H | Cl |
| Cl | H | CH₃ | Cl | H | SO₂CF₃ | H | H |
| Cl | H | CH₃ | Cl | H | SOCF₃ | H | H |
| Cl | H | CH₃ | Cl | Cl | Cl | H | Cl |
| Cl | H | CF₃ | Cl | H | OCF₃ | H | Cl |
| Cl | CH₃ | CF₃ | Cl | Cl | Cl | H | H |
| Cl | H | C₄H₉ | Cl | Cl | CF₃ | H | Cl |
| Cl | CH₃ | C₄F₉ | Cl | H | SCF₃ | H | Cl |
| Cl | H | CH₃ | CF₃ | H | CF₃ | H | H |
| Cl | H | CH₃ | Cl | H | NO₂ | H | Cl |
| Cl | H | CH₃ | NO₂ | H | NO₂ | H | H |
| Cl | H | CH₃ | Cl | H | CH₃ | H | Cl |
| Cl | H | CF₃ | Cl | H | CH(CH₃)₂ | H | Cl |
| Cl | H | CH₂Cl | Cl | H | C(CH₃)₃ | H | Cl |
| Cl | H | CH₃ | Br | H | OCF₃ | H | Cl |
| Br | H | CH₃ | Cl | H | CF₃ | H | Br |

TABLE 1-continued (I)

Structure: pyrazole with R¹ at 4-position, N-R² and SO₂-R³ at 5-position N, and N1-phenyl substituted with R⁴, R⁵, R⁶, R⁷, R⁸.

| R¹ | R² | R³ | R⁴ | R⁵ | R⁶ | R⁷ | R⁸ |
|---|---|---|---|---|---|---|---|
| Br | CH₃ | CH₃ | Cl | Cl | CF₃ | H | Cl |
| Br | H | CH₃ | Cl | F | CF₃ | Cl | Cl |
| Br | H | CH₃ | Cl | F | CF₃ | F | F |
| Br | H | CH₃ | F | F | CF₃ | F | F |
| Br | H | CH₃ | Cl | F | Cl | F | Cl |
| Br | H | C₂H₅ | Cl | H | Br | H | Cl |
| Br | H | CH₃ | F | F | F | F | F |
| Br | C₂H₅ | CH₂Cl | Cl | H | CF₃ | H | H |
| Br | (CH₂)₂OH | CF₃ | Cl | Cl | Cl | H | H |
| Br | H | CH₃ | Cl | H | OCF₃ | H | Cl |
| Br | H | C₄H₉ | Cl | H | SCF₃ | H | Cl |
| Br | CH₃ | CH₃ | Cl | Cl | OCF₃ | H | Cl |
| Br | H | (CH₂)₂Cl | Cl | Cl | SCF₃ | H | Cl |
| Br | H | CF₃ | Cl | Cl | Cl | H | Cl |
| Br | H | CF₃ | Cl | H | Cl | H | Cl |
| Br | CH(CH₃)₂ | CH₃ | Br | H | Br | H | Br |
| Br | H | C₄F₉ | Br | H | CH₃ | H | H |
| Br | H | C₄H₉ | Cl | H | OCF₂CHF₂ | H | H |
| Br | H | CH₃ | Cl | H | SO₂CCl₂F | H | Cl |
| Br | H | CH₃ | Cl | H | SO₂CClF₂ | H | Cl |
| Br | CH₃ | CH₂Cl | Br | H | SCF₃ | H | Br |
| Br | H | C₄H₉ | Br | H | SCF₃ | H | H |
| Br | H | CH₃ | CF₃ | F | Cl | H | Cl |
| Br | CH₃ | CH₃ | CF₃ | H | Cl | H | H |
| Br | H | C₄H₉ | CF₃ | H | Br | H | H |
| Br | H | CH₃ | Cl | F | CN | F | Cl |
| Br | H | CH₃ | F | F | CN | F | F |
| Br | H | CH₃ | F | Cl | F | Cl | F |
| Br | H | phenyl | Cl | Cl | CF₃ | H | Cl |
| Br | CH₃ | phenyl | Cl | H | OCF₃ | H | H |
| Br | CH₃ | 4-Cl-phenyl | Cl | H | CF₃ | H | Cl |
| Br | H | 4-NO₂-phenyl | Cl | H | CF₃ | H | Cl |
| Br | CH₃ | CH₂Cl | Cl | H | CF₃ | H | H |
| Br | C₃H₇ | CH₃ | Cl | Cl | CF₃ | H | Cl |
| Br | (CH₂)₂OH | C₄H₉ | Cl | H | SO₂CF₃ | H | Cl |
| Br | H | CH₃ | Cl | H | SO₂CF₃ | H | H |
| Br | H | CH₃ | Cl | H | SOCF₃ | H | H |
| Br | H | CH₃ | Cl | Cl | Cl | H | Cl |
| Br | H | CF₃ | Cl | H | OCF₃ | H | Cl |
| Br | CH₃ | CF₃ | Cl | Cl | Cl | H | H |
| Br | H | C₄F₉ | Cl | Cl | CF₃ | H | Cl |
| Br | CH₃ | C₄F₉ | Cl | H | SCF₃ | H | Cl |
| Br | H | CH₃ | CF₃ | H | CF₃ | H | H |
| Br | H | CH₃ | Cl | H | NO₂ | H | Cl |
| Br | H | CH₃ | NO₂ | H | NO₂ | H | H |
| Br | H | CH₃ | Cl | H | CH₃ | H | Cl |

TABLE 1-continued

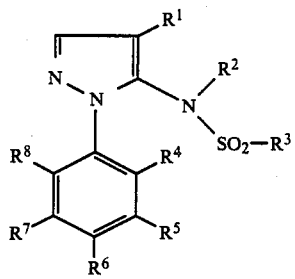

| R¹ | R² | R³ | R⁴ | R⁵ | R⁶ | R⁷ | R⁸ |
|---|---|---|---|---|---|---|---|
| Br | H | CF$_3$ | Cl | H | CH(CH$_3$)$_2$ | H | Cl |
| Br | H | CH$_2$Cl | Cl | H | C(CH$_3$)$_3$ | H | Cl |
| Br | H | CH$_3$ | Br | H | OCF$_3$ | H | Cl |
| I | H | CH$_3$ | Cl | H | CF$_3$ | H | Br |
| I | CH$_3$ | CH$_3$ | Cl | Cl | CF$_3$ | H | Cl |
| I | H | CH$_3$ | Cl | F | CF$_3$ | Cl | Cl |
| I | H | CH$_3$ | Cl | F | CF$_3$ | F | F |
| I | H | CH$_3$ | F | F | CF$_3$ | F | F |
| I | H | CH$_3$ | Cl | F | Cl | F | Cl |
| I | H | C$_2$H$_5$ | Cl | H | Br | H | Cl |
| I | H | CH$_3$ | F | F | F | F | F |
| I | C$_2$H$_5$ | CH$_2$Cl | Cl | H | CF$_3$ | H | H |
| I | (CH$_2$)$_2$OH | CF$_3$ | Cl | Cl | Cl | H | H |
| I | H | CH$_3$ | Cl | H | OCF$_3$ | H | Cl |
| I | H | C$_4$H$_9$ | Cl | H | SCF$_3$ | H | Cl |
| I | CH$_3$ | CH$_3$ | Cl | Cl | OCF$_3$ | H | H |
| I | H | (CH$_2$)$_2$Cl | Cl | Cl | SCF$_3$ | H | Cl |
| I | H | CF$_3$ | Cl | Cl | Cl | H | Cl |
| I | H | CF$_3$ | Cl | H | Cl | H | Cl |
| I | CH(CH$_3$)$_2$ | CH$_3$ | Br | H | Br | H | Br |
| I | H | C$_4$F$_9$ | Br | H | CH$_3$ | H | H |
| I | H | C$_4$H$_9$ | Cl | H | OCF$_2$CHF$_2$ | H | H |
| I | H | CH$_3$ | Cl | H | SO$_2$CCl$_2$F | H | Cl |
| I | H | CH$_3$ | Cl | H | SO$_2$CClF$_2$ | H | Cl |
| I | CH$_3$ | CH$_2$Cl | Br | H | SCF$_3$ | H | Br |
| I | H | C$_4$H$_9$ | Br | H | SCF$_3$ | H | H |
| I | H | CH$_3$ | CF$_3$ | F | Cl | H | Cl |
| I | CH$_3$ | CH$_3$ | CF$_3$ | H | Cl | H | H |
| I | H | C$_4$H$_9$ | CF$_3$ | H | Br | H | H |
| I | H | CH$_3$ | Cl | F | CN | F | Cl |
| I | H | CH$_3$ | F | F | CN | F | F |
| I | H | CH$_3$ | F | Cl | F | Cl | F |
| I | H |  | Cl | Cl | CF$_3$ | H | Cl |
| I | CH$_3$ |  | Cl | H | OCF$_3$ | H | H |
| I | CH$_3$ | 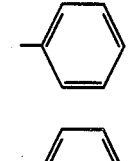 | Cl | H | CF$_3$ | H | Cl |
| I | H | 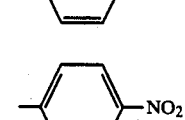 | Cl | H | CF$_3$ | H | Cl |
| I | CH$_3$ | CH$_2$Cl | Cl | H | CF$_3$ | H | H |
| I | C$_3$H$_7$ | CH$_3$ | Cl | Cl | CF$_3$ | H | Cl |
| I | (CH$_2$)$_2$OH | C$_4$H$_9$ | Cl | H | SO$_2$CF$_3$ | H | Cl |
| I | H | CH$_3$ | Cl | H | SO$_2$CF$_3$ | H | H |
| I | H | CH$_3$ | Cl | H | SOCF$_3$ | H | H |
| I | H | CH$_3$ | Cl | Cl | Cl | H | Cl |
| I | H | CF$_3$ | Cl | H | OCF$_3$ | H | Cl |
| I | CH$_3$ | CF$_3$ | Cl | Cl | Cl | H | H |
| I | H | C$_4$F$_9$ | Cl | Cl | CF$_3$ | H | Cl |
| I | CH$_3$ | C$_4$F$_9$ | Cl | H | SCF$_3$ | H | Cl |

TABLE 1-continued (I)

| R¹ | R² | R³ | R⁴ | R⁵ | R⁶ | R⁷ | R⁸ |
|----|----|-----|------|----|--------|----|----|
| I | H | CH₃ | CF₃ | H | CF₃ | H | H |
| I | H | CH₃ | Cl | H | NO₂ | H | Cl |
| I | H | CH₃ | NO₂ | H | NO₂ | H | H |
| I | H | CH₃ | Cl | H | CH₃ | H | Cl |
| I | H | CF₃ | Cl | H | CH(CH₃)₂ | H | Cl |
| I | H | CH₂Cl | Cl | H | C(CH₃)₃ | H | Cl |
| I | H | CH₃ | Br | H | OCF₃ | H | Cl |

If, for example, 5-amino-1-(2,6-dichloro-4-trifluoromethyl)-phenyl-pyrazole and methanesulphonyl chloride are used as starting substances, the course of the reaction in process (a) according to the invention can be represented by the following equation:

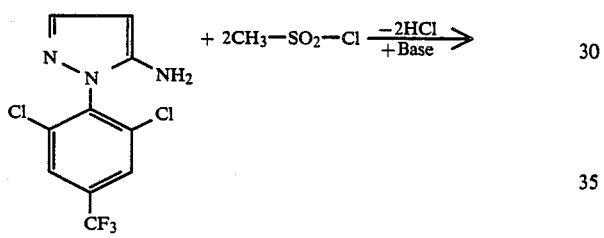

If, for example, 5-[N,N-bis-(methanesulphonyl)-amino]-1-(2,6-dichloro-4-trifluoromethyl)-phenyl-pyrazole and ammonia are used as starting substances, the course of the reaction in process (b) according to the invention can be represented by the following equation:

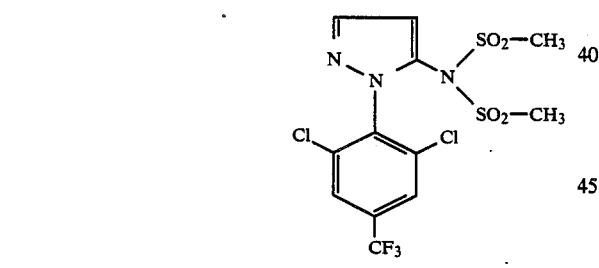

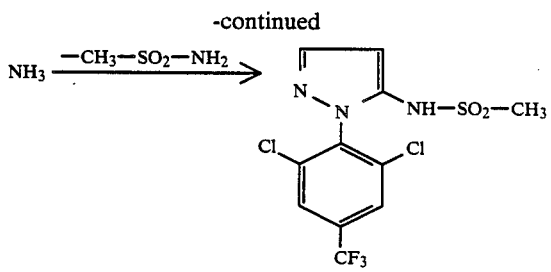

If, for example, 5-methanesulphonamido-1-(2,6-dichloro-4-trifluoromethyl)-phenyl-pyrazole and nitric acid are used as starting substances, the course of the reaction in process (c) according to the invention can be represented by the following equation:

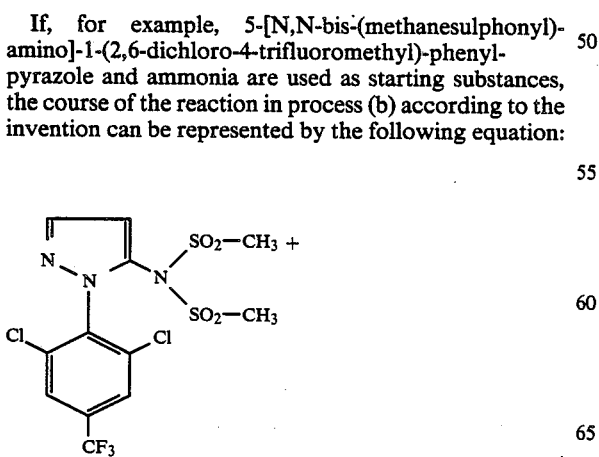

If, for example, 4-nitro-5-methanesulphonamido-1-(2,6-dichloro-4-trifluoromethyl)phenyl-pyrazole and methyl iodide are used as starting substances, the course of the reaction in process (d) (i) according to the invention can be represented by the following equation:

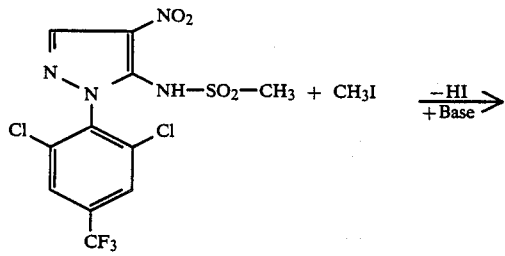

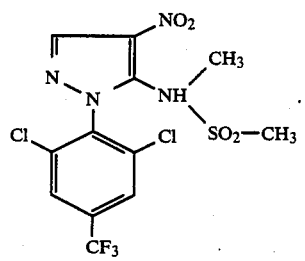

If, for example, 4-chloro-5-methane-sulphonamido-1-(2-chloro-4-trifluoromethyl)-phenyl-pyrazole and isopropylamine are used as starting substances, the course of the reaction in process (d) (ii) according to the invention can be represented by the following equation:

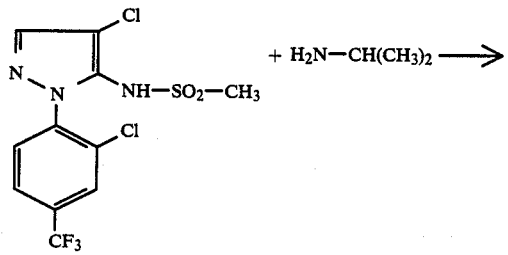

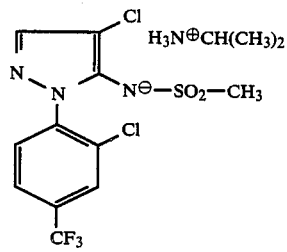

Formula (II) provides a general definition of the 5-aminopyrazoles required as starting substances for carrying out process (a) according to the invention. In this formula (II), $R^4$, $R^5$, $R^6$, $R^7$ and $R^8$ preferably represent those substituents which have already been mentioned as preferred for these radicals in connection with the description of the substances of the formula (I) according to the invention.

The 5-aminopyrazoles of the formula (II) are known in some cases (compare, for example, J. Org. Chemistry, 36, 2972–2974 (1971); J. Heterocycl. Chem., 7, 345–349 (1970); and C.A., 62, 13 137c).

The substituted 5-aminopyrazoles of the formula (II) which are not yet known are, however, the subject of a previous patent application which has been filed by the Applicant Company (German Pat. No. 3,402,308 of Jan. 24, 1984).

They are obtained, for example, by a process in which phenylhydrazines of the formula (VII)

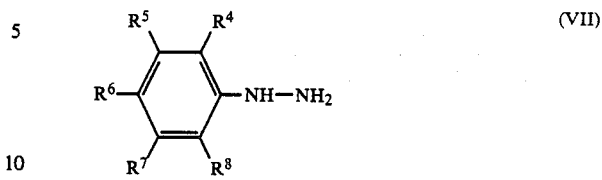

in which $R^4$, $R^5$, $R^6$, $R^7$ and $R^8$ have the abovementioned meaning, are either reacted initially in a first stage with 2-halogeno-acrylonitriles of the formula (VIIIa)

in which Hal represents halogen, in particular chlorine or bromine, or with 2,3-dihalogenopropionitriles of the formula (VIIIb)

in which Hal' represents halogen, in particular chlorine or bromine, if appropriate in the presence of a diluent, such as, for example, methanol, and if appropriate in the presence of a reaction auxiliary, such as, for example, sulphuric acid, at temperatures between −30° C. and +50° C., to give the phenylhydrazine derivatives of the formula (IX)

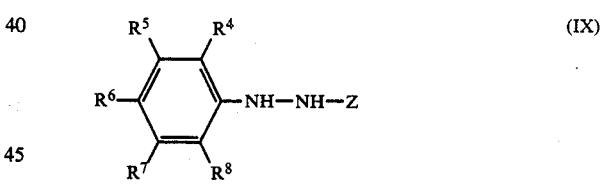

in which
$R^4$, $R^5$, $R^6$, $R^7$ and $R^8$ have the abovementioned meaning and
Z represents one of the radicals

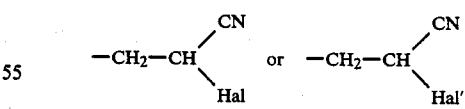

wherein Hal and Hal' represent identical or different halogen atoms, and these are cyclized in a 2nd stage, if appropriate in the presence of a diluent, such as, for example, methanol, and if appropriate in the presence of an acid-binding agent, such as, for example, sodium carbonate, at temperatures between 50° C. and 150° C., or the phenylhydrazines of the formula (VII) are cyclized directly in one reaction step, without isolation of the intermediate stage of the formula (IX), if appropriate in the presence of a diluent, such as, for example, ethanol, at temperatures between 50° C. and 150° C.

directly, to give the 5-amino-pyrazoles of the formula (II)

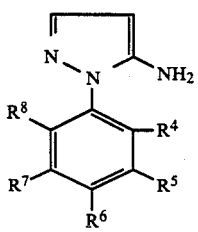

in which $R^4$, $R^5$, $R^6$, $R^7$ and $R^8$ have the abovementioned meaning.

The phenylhydrazines of the formula (VII) are known in most cases or they can be prepared in a simple manner by a process analogous to known processes (compare, for example, Houben-Weyl "Methoden der organischen Chemie" ("Methods of Organic Chemistry") Volume X,2, Thieme Verlag Stuttgart 1967), in which, for example, the known anilines of the formula (X)

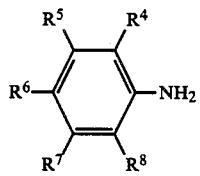

in which $R^4$, $R^5$, $R^6$, $R^7$ and $R^8$ have the abovementioned meaning, are reacted with sodium nitrite in the presence of an acid, such as, for example, sulphuric acid, and the products are then reacted with tin(II) chloride, also in the presence of an acid, such as, for example, hydrochloric acid, at temperatures between $-20°$ C. and $+80°$ C.

The 2-halogeno-acrylonitriles of the formula (VIIIa) and the 2,3-dihalogeno-propionitriles of the formula (VIIIb) are likewise known (compare, for example, *J. Prakt. Chemie*, 321, 93 (1979); *J. Heterocyclic Chem.*, 19, 1265 (1982); and *J. Heterocyclic Chem.*, 19, 1267 (1982)).

Formula (III) provides a general definition of the sulphonyl chlorides furthermore required as starting substances for carrying out process (a) according to the invention. Preferred compounds of the formula (III) are those in which $R^3$ preferably represents those radicals which have already been mentioned as preferred for this substituent in the description of the substances of the formula (I) according to the invention.

The sulphonyl chlorides of the formula (III) are generally known compounds of organic chemistry.

Formula (Ia) provides a general definition of the bisulphonylamines required as starting substances for carrying out process (b) according to the invention. In this formula (Ia), $R^3$, $R^4$, $R^5$, $R^6$, $R^7$ and $R^8$ preferably represent those substituents which have already been mentioned as preferred for those radicals in the description of the substances of the formula (I) according to the invention.

The bisulphonylamines are substances according to the invention and can be obtained with the aid of process (a) according to the invention.

Formula (Ib) provides a general definition of the 5-sulphonamido-pyrazoles required as starting substances for carrying out process (c) according to the invention. In this formula (Ib), $R^3$, $R^4$, $R^5$, $R^6$, $R^7$ and $R^8$ preferably represent those substituents which have already been mentioned as preferred for these radicals in connection with the description of the substances of the formula (I) according to the invention. $R^{2'}$ preferably represents hydrogen or a radical $-R^3-SO_2-$.

The 5-sulphonamido-pyrazoles of the formula (Ib) are substances according to the invention and can be obtained with the aid of process (a) or (b) according to the invention.

Formula (IV) provides a general definition of the electrophilic agents furthermore required as starting substances for carrying out process (a) according to the invention. In this formula (IV), $R^{1'}$ preferably represents chlorine, bromine, iodine, nitroso or nitro. E preferably represents halogen, in particular chlorine or bromine, hydroxyl, alkyl, alkyl- or aryl-sulphonyloxy, alkanoyloxy or aroyloxy. Electrophilic reagents which can furthermore be used are sulphuryl chloride, phosphorus pentachloride, nitrating acid and other substances which can usually be employed for electrophilic substitution reactions. The electrophilic agents of the formula (IV), like the other customary electrophilic reagents, are generally known compounds.

Formula (Ic) provides a general definition of the 5-sulphonamido-pyrazoles required as starting substances for carrying out process (d) according to the invention. In this formula (Ic), $R^1$, $R^3$, $R^4$, $R^5$, $R^6$, $R^7$ and $R^8$ preferably represent those substituents which have already been mentioned as preferred for these radicals in connection with the description of the substances of the formula (I) according to the invention.

The 5-sulphonamido-pyrazoles of the formula (Ic) are compounds according to the invention and can be obtained with the aid of process (a), (b) or (c) according to the invention.

Formula (V) provides a general definition of the alkylating agents furthermore required as starting compounds for carrying out process (d) (i) according to the invention. In this formula (V), $R^{2''}$ preferably represents straight-chain or branched alkyl with 1 to 8 carbon atoms, in particular methyl, ethyl, n- or i-propyl or n-, i-, s- or t-butyl. E' preferably represents chlorine, bromine or iodine, p-toluenesulphonyloxy or alkoxysulphonyloxy, in particular chlorine, bromine, iodine, methoxysulphonyloxy or ethoxysulphonyloxy. The alkylating agents of the formula (V) are generally known compounds of organic chemistry.

Formula (VI) provides a general definition of the salt-forming agents furthermore required as starting substances for carrying out process (d) (ii) according to the invention. Salt-forming agents which are preferably used are alkali metal, alkaline earth metal, ammonium or transition metal hydroxides, oxides, carbonates, bicarbonates or readily soluble chlorides, sulphates, phosphates or nitrates, such as, for example, sodium, potassium or calcium hydroxide, carbonate or bicarbonate, calcium chloride, barium chloride, copper sulphate, nickel chloride or cobalt nitrate, or alkylamines, such as triethylamine, isopropylamine, diisopropylamine or butylamine.

Possible diluents for carrying out process (a) according to the invention are inert organic solvents.

Solvents which are preferably used are aliphatic or aromatic, optionally halogenated hydrocarbons, such as, for example, benzine, benzene, toluene, xylene, pentane, hexane heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran, ethylene glycol diethyl ether or ethylene glycol dimethyl ether, ketones, such as acetone, butanone, methyl isopropyl ketone or methyl isobutyl ketone, esters, such as ethyl acetate, nitriles, such as acetonitrile or propionitrile, and amides, such as dimethylformamide, diethylformamide, dimethylacetamide, N-methylpyrrolidone or or hexamethylphosphoric acid triamide.

Possible acid-binding agents for carrying out preparation process (a) are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or also tertiary amines, such as, for example, triethylamine, N,N-dimethylaniline, pyridine, 4-(N,N-dimethylamino)-pyridine, diazabicylooctane (DABCO), diazabicyclononene (DBN) or diazabicycloundecene (DBU).

The reaction temperatures can be varied within a substantial range in carrying out preparation process (a). The reaction is in general carried out between $-20°$ C. and 150° C., preferably between 0° C. and $+100°$ C.

For carrying out preparation process (a), in general 1.0 to 20 moles, preferably 1.0 to 15 moles, of sulphonyl chloride of the formula (III) and, if appropriate, 1.0 to 3.0 moles, preferably 1.0 to 2.0 moles, of acid-binding agent are employed per mole of 5-amino-pyrazole of the formula (II). The reaction is carried out and the reaction products of the formula (I) are worked up and isolated in the generally customary manner.

Possible diluents for carrying out process (b) according to the invention are polar organic solvents or mixtures thereof with water. Solvents which are preferably used are alcohols, such as methanol, ethanol or propanol, or mixtures thereof with water.

Possible basic reaction participants in carrying out process (b) according to the invention are all the usual inorganic or organic bases. Bases which are preferably used are amines or ammonia solutions, or alkali metal carbonates or bicarbonates, such as sodium or potassium carbonate or sodium bicarbonate.

The reaction temperatures can be varied within a substantial range in carrying out preparation process (b) according to the invention. The reaction is in general carried out between 0° C. and 80° C., preferably between 20° C. and 40° C.

For carrying out process (b) according to the invention, in general 1.0 to 30.0 moles, preferably 1.0 to 15.0 moles, of base are employed per mole of bis-sulphonylamine of the formula (Ia).

The reaction mixture is stirred in a suitable diluent until the starting substance is no longer detectable in a chromatographic check (30 minutes to 20 hours). The reaction products of the formula (I) are worked up by customary methods.

Possible diluents for carrying out preparation process (c) are all the solvents which can usually be employed for such electrophilic substitution reactions. The acids or mixtures possible as reagents, such as, for example, sulphuric acid, nitric acid, sulphuryl chloride or nitrating acid, are preferably simultaneously used as the diluent. If appropriate, inert organic solvents, such as, for example, glacial acetic acid, ethanol or chlorinated hydrocarbons, such as methylene chloride, chloroform or carbon tetrachloride, are also possible as the diluent.

Possible catalysts or reaction auxiliaries for carrying out preparation process (c) are likewise the catalysts which are customary for such reactions; hydrochloric acid, sulphuric acid, ion-II chloride or other Lewis acids or acetic anhydride are preferred.

The reaction temperatures can be varied within a substantial range in carrying out preparation process (c). In general, the reaction is carried out between $-50°$ C. and $+200°$ C., preferably between $-20°$ C. and $+150°$ C.

For carrying out preparation process (c), in general 1.0 to 10.0 moles, preferably 1.0 to 5.0 moles, of electrophilic agent of the formula (IV) and, if appropriate, 0.1 to 10 moles of catalyst or reaction auxiliary are employed per mole of 5-amino-pyrazole of the formula (Ib). The reaction is carried out and the reaction products of the formula (I) are worked up and isolated in the generally customary manner.

Possible diluents for carrying out preparation process (d)(i) are likewise inert organic solvents. The solvents mentioned for preparation process (a) are preferably used.

Possible acid-binding agents or catalyst for carrying out preparation process (d)(i) are all the organic or inorganic bases which can usually be employed. The bases mentioned to process (a) are preferably used.

The reaction temperatures can likewise be varied within a substantial range in preparation process (d)(i). The reaction is in general carried out between $-20°$ C. and $+120°$ C., preferably between 0° C. and $+90°$ C.

For carrying out preparation process (d)(i), in general 1.0 to 5.0 moles, preferably 1.0 to 3.0 moles, of alkylating agent of the formula (V) and, if appropriate, 1.0 to 5.0 moles, preferably 1.0 to 3.0 moles, of acid-binding agent are employed per mole of 5-sulphonamidopyrazole of the formula (Ic). The reaction is carried out and the reaction products of the formula (I) are worked up and isolated in the generally customary manner.

Possible diluents for carrying out preparation process (d)(ii) are polar organic solvents, water or aqueous mixtures. Diluents which are preferably used are alcohols, such as, for example, methanol, ethanol or propanol, aqueous mixtures thereof or pure water.

The reaction temperatures can likewise be varied within a substantial range in carrying out preparation process (d)(ii). The reaction is in general carried out between 0° C. and $+80°$ C., preferably between $+20°$ C. and $+40°$ C.

For carrying out process (d)(ii) according to the invention, in general 1.0 to 10 moles, preferably 1.0 to 5.0 moles, of salt-forming agent of the formula (VI) or amine are employed per mole of 5-sulphonamidopyrazole of the formula (Ic).

To prepare the sodium, potassium or ammonium salts, a compound of the formula (Ic) is reacted with sodium hydroxide, potassium hydroxide or ammonium, hydroxide or an amine in aqueous solution or an organic solvent, such as acetone, methanol, ethanol or dimethylformamide, and the salts are isolated by filtration or by evaporation of the solution and, if appropriate, purified by recrystallisation.

The calcium, barium, magnesium, manganese, copper, nickel, tin, iron and cobalt salts are prepared from the sodium salts by treatment with a corresponding inorganic metal salt, for example calcium chloride, barium chloride, copper sulphate, nickel chloride or cobalt nitrite. The calcium salts can also be prepared by treatment of a compound of the formula (Ic) with calcium hydroxide.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, LoliumBromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Arrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used here particularly successfully for selectively combating monocotyledon and dicotyledon weeds in monocotyledon crops, such as, for example, wheat.

The active compunds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable, for example, ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable, for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable, for example, non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products. As dispersing agents there are suitable, for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one, for combating weeds in sugar beet, and 4-amino-6-(1,1-dimethylethyl)-3-methylthio-1,2,4-triazin-5(4H)-one, for combating weeds in soya bean.

Mixtures with N,N-dimethyl-N'-(3-trifluoromethylphenyl)-urea, N,N-dimethyl-N'-(3-chloro-4-methylphenyl)-urea; N,N-dimethyl-N'-(4-isopropylphenyl)-urea; 2,4-dichlorophenoxyacetic acid; 2,4-dichlorophenoxypropionic acid; (2-methyl-4-chlorophenoxy)-acetic acid; (4-chloro-2-methylphenoxy)-propionic acid; 2-benzyloxy-ethyl, trimethylsilyl-methyl or 2,2-diethoxyethyl 2-[4-(3,5-dichloropyrid-2-yloxy)-phenoxy]-propionate; methyl 5-(2,4-dichlorophenoxy)-2-nitrobenzoate; 3,5-diiodo-4-hydroxybenzonitrile; 3-isopropyl-2,1,3-benzothiadiazin-4-one 2,2-dioxide; 2-chloro-n-<[(4-methoxy-6-methyl-1,3,5-triazin-2-yl)-amino]-carbonyl>-benzenesulphonamide, 4-ethylamino-2-t-butylamino-6-methylthio-s-triazine; N-methyl-2-(benzothiazol-2-yloxy)-acetamide; N-(1-ethylpropyl)-3,4-dimetyl-2,6-dinitroaniline; α-chloro-1',6'-diethyl-N-(2-propoxyethyl)-acetanilide or 2,3,3-trichloroallyl N,N-diisopropylthiocarbamate, are also possible. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulatins or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 g of active compound per hectare of soil surface, preferably between 0.05 and 5 kg per ha.

The preparation and use of the active compounds according to the invention can be seen from the following non-limiting examples.

PREPARATION OF EXAMPLES

Example 1

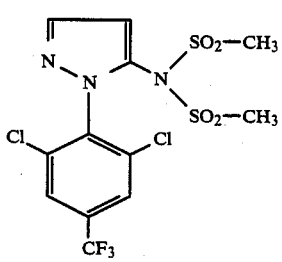

According to process (a):

5.9 (0.02 mole) of 5amino-1-(2,6-dichloro-4-trifluoromethylphenyl)-pyrazole are dissolved in 40 ml of methylene chloride, and 4 ml ($\hat{=}3.9$ g$\hat{=}0.047$ mole) of methanesulphonyl chloride are added in sucession. The mixture is heated under reflux for 8 hours, cooled and washed successively with water, dilute hydrochloric acid and saturated bicarbonate solution. The organic phase is dried over magnesium sulphate and evaporated in vacuo. 7.6 g of crude product consisting of mono- and bimesylated aminopyrazole are obtained. The entire crude product is stirred in about 20 ml of ethanol. The insoluble residue is filtered off, washed and dried.

1.3 g (14% of theory) of 5-bis-(methanesulphone)imido-1-(2,6-dichloro-4-trifluoromethylphenyl)-pyrazole of melting point 196°-198° C. are obtained.

EXAMPLE 2

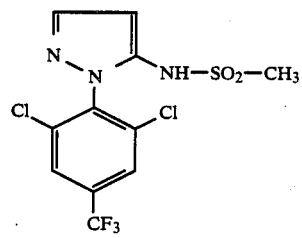

According to process (a):

A small amount of active charcoal is added to the ethanol-soluble filtrate from Example 1, the mixture is filtered and the filtrate is evaporated.

A brownish oil which slowly crystalizes out is obtained. Yield: 5.0 g (67% of theory) of 5-methane-sulphonamido-1-(2,6-dichloro-4-trifluoromethylphenyl)-pyrazole of melting point 64°-67° C.

According to process (b):

2 g (4.4 mmol) of 5-bis-(methanesulphone)-imido-1-(2,6-dichloro-4-trifluoromethylphenyl)-pyrazole are suspended in a mixture of 5 ml of ethanol and 5 ml of concentrated ammonia solution and the suspension is stirred at room temperature per 16 hours; the suspension thereby dissolves. The solvent is distilled off in vacuo and the oily residue is taken up in methylene chloride and dilute hydrochloric acid. The organic phase is separated off, washed with sodium chloride solution and dried over magnesium sulphate. After evaporation in vacuo, 1.5 g (91% of theory) of 5-methanesulphonamido-1-(2,6-dichloro-4-trifluoromethylphenyl)-pyrazole of melting point 65°-67° C. are obtained.

Example 3

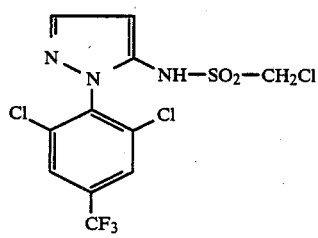

According to process (a):

10 g (0.034 mole) of 5-amino-1-(2,6-dichloro-4-trifluoromethylphenyl)-pyrazole are dissolved in 35 ml of pyridine. 21.4 g (0.068 mole) of 47% chloromethanesulphonyl chloride, dissolved in 1,2-dichlorobenzene, are added dropwise at 0° C. to 5° C. The mixture is stirred for five hours, during which the temperature slowly rises to 20° C. The mixture is then poured into ice-water and extracted with methylene chloride. The organic phase is separated off, washed with dilute hydrochloric acid and extracted three times with 100 ml of saturated sodium bicarbonate solution. The combined aqueous phases are brought to pH 1 with 10% strength hydrochloric acid and the product which has precipitated is taken up in methylene chloride. The methylene chloride phase is separated off, washed with saturated sodium chloride solution, dried over magnesium sulphate and concentrated. 8.7 g (63% of theory) of 5-chloromethanesulphonamido-1-(2,6-dichloro-4-trifluoromethylphenyl)-pyrazole of melting point 63°-66° C. are obtained.

Example 4

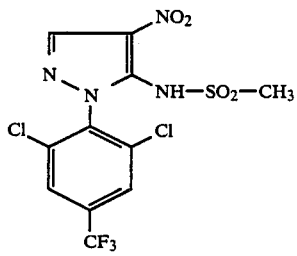

According to process (c):

3.2 g (8.6 mmol) of 5-methanesulphonamido-1-(2,6-dichloro-4-trifluoromethylphenyl)-pyrazole are dissolved in 10 ml of glacial acetic acid, and 0.8 ml (8.6 mmol) of acetic anhydride and 0.4 ml (9.3 mmol) of 98% strength nitric acid are added in succession at 10° C. to 15° C. The mixture is stirred at room temperature for 16 hours, concentrated in vacuo and taken up in 50 ml of methylene chloride. This solution is extracted three times with 50 ml of saturated sodium bicarbonate solution each time. The combined aqueous phases are brought to pH 1 with dilute hydrochloric acid, the precipitate formed is dissolved in methylene chloride, and the aqueous phase is removed. The organic phase is washed with sodium chloride solution and dried over magnesium sulphate. After the solvent has been stripped off in vacuo, 2.8 g (78% of theory) of 5-methanesulphonamido-4-nitro-1-(2,6-dichloro-4-trifluoromethylphenyl)-pyrazole of melting point 163° C. are obtained.

Example 5

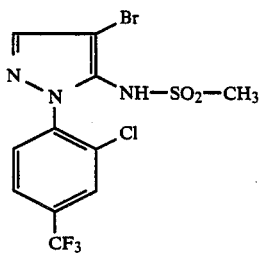

According to process (c):

3.4 g (0.01 mole) of 5-methanesulphonamido-1-(2-chloro-4-trifluoromethylphenyl)-pyrazole are dissolved in 20 ml of methylene chloride, with 0.52 ml (0.01 mole) of bromine, dissolved in 5 ml of methylene chloride, is added. When the addition has ended, the mixture is subsequently stirred for one hour, diluted with 20 ml of methylene chloride and washed successively with bicarbonate, thiosulphate and sodium chloride solution. The organic solution is then dried over magnesium sulphate and concentrated in vacuo.

3.4 g (91% of theory) of 4-bromo-5-methanesulphonamido-1-(2-chloro-4-trifluoromethylphenyl)-pyrazole of melting point 63°-65° C. are obtained.

Example 6

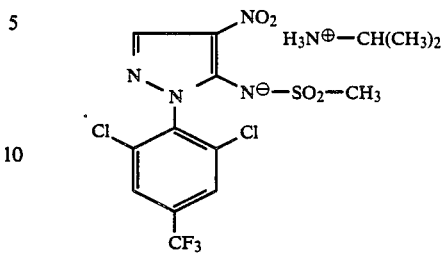

According to process (d-β):

3 g (7.2 mmol) of 5-methanesulphonamido-4-nitro-1-(2,6-dichloro-4-trifluoromethylphenyl)-pyrazole are suspended in 40 ml of ethanol, and 1.1 ml (10.7 mmol) of a 70% strength alcoholic isopropylamine solution are added. The clear solution formed is concentrated in vacuo.

3.4 g (100% of theory) of 5-methananesulphonamido-4-nitro-1-(2,6-dichloro-4-trifluoromethylphenyl)-pyrazole isopropylammonium salt of melting point 188° C. are obtained.

Example 7

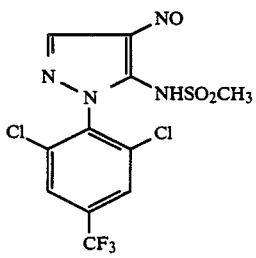

According to process (c):

1.5 g (4.0 mmol) of 5-methanesulphonamido-1-(2,6-dichloro-4-trifluoromethylphenyl)-pyrazole are dissolved in 20 ml of ethanol, the solution is cooled to 0° C. to 5° C. and 1 ml of cold ethyl nitrite and 1 ml of concentrated hydrochloric acid are added. The mixture is stirred at 0° C. to 5° C. for about 6 hours and at room temperature for 14 hours. The solvent is distilled off in vacuo, the residue is taken up in 20 ml of methylene chloride and 10 ml of water, the aqueous phase is brought up to pH 3 with sodium acetate solution and the organic phase is then separated off, washed with sodium chloride solution and dried over magnesium sulphate. After removing the solvent in vacuo, 1.4 g (87% of theory) of 5-methanesulphonamido-4-nitroso-1-(2,6-dichloro-4-trifluoromethylphenyl)-pyrazole of melting point 151° C. -153° C. are obtained.

The 5-sulphonamido-1-aryl-pyrazoles of the general formula (I)

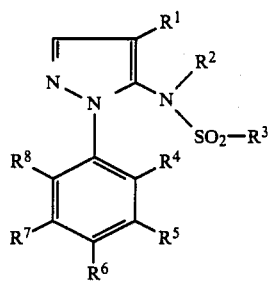

(I)

listed in the following table are obtained in a corresponding manner and in accordance with the general preparation data.

Use Examples

The compound shown below was used as the comparison substance in the following use examples:

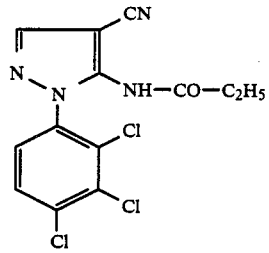

(A)

4-Cyano-5-propionamido-1-(2,3,4-trichlorophenyl)-pyrazole (known from DE-OS (German Published Specification) No. 3,226,513)

TABLE 2

| Example No. | $R^1$ | $R^2$ | $R^3$ | $R^4$ | $R^5$ | $R^6$ | $R^7$ | $R^8$ | Melting point (°C.) |
|---|---|---|---|---|---|---|---|---|---|
| 8 | H | H | phenyl | Cl | H | $CF_3$ | H | H | 150 |
| 9 | H | H | phenyl | Cl | H | $CF_3$ | H | Cl | 126 |
| 10 | H | H | $CH_3$ | Cl | H | $CF_3$ | H | H | 137–138 |
| 11 | H | H | $CH_3$ | Cl | Cl | $CF_3$ | H | Cl | Glass IR (cm$^{-1}$): $\nu_{symSO2}$ = 1165 |
| 12 | H | H | $CH_3$ | Cl | H | $-SO_2CF_3$ | H | Cl | Glass IR (cm$^{-1}$): $\nu_{symSO2}$ = 1165 |
| 13 | H | H | $CH_3-(CH_2)_3-$ | Cl | H | $CF_3$ | H | Cl | Oil IR (cm$^{-1}$): $\nu_{symSO2}$ = 1145 |
| 14 | $NO_2$ | H | phenyl | Cl | H | $CF_3$ | H | Cl | 180–181 |
| 15 | $NO_2$ | H | phenyl | Cl | H | $CF_3$ | H | H | 150–151 |
| 16 | $NO_2$ | H | $CH_3$ | Cl | H | $CF_3$ | H | H | 64 |
| 17 | $NO_2$ | H | $CH_3$ | Cl | Cl | $CF_3$ | H | Cl | 76 |
| 18 | $NO_2$ | H | $CH_3-(CH_2)_3-$ | Cl | H | $CF_3$ | H | Cl | 155–157 |
| 19 | $NO_2$ | H | $ClCH_2-$ | Cl | H | $CF_3$ | H | Cl | 172–175 |
| 20 | $NO_2$ | H | $CH_3$ | Cl | H | $-SO_2CF_3$ | H | Cl | 209–211 |
| 21 | $NO_2$ | H | $CF_3$ | Cl | H | $CF_3$ | H | Cl | 133–138 (decomposition) |
| 22 | H | H | $CF_3$ | Cl | H | $CF_3$ | H | Cl | >300 |
| 23 | $NO_2$ | $K^\oplus$ | $CH_3$ | Cl | H | $CF_3$ | H | Cl | >270 (decomposition) |
| 24 | $NO_2$ | ½ $Mg^{2\oplus}$ | $CH_3$ | Cl | H | $CF_3$ | H | Cl | 150–155 |
| 25 | $NO_2$ | $H_3N^\oplus-CH(CH_3)_2$ | $CH_3-(CH_2)_3-$ | Cl | H | $CF_3$ | H | Cl | 72 |
| 26 | $NO_2$ | $H_3N^\oplus-CH(CH_3)_2$ | $ClCH_2-$ | Cl | H | $CF_3$ | H | Cl | 128–129 |
| 27 | $NO_2$ | $H_3N^\oplus-CH(CH_3)_2$ | $CF_3$ | Cl | H | $CF_3$ | H | Cl | 53–60 |
| 28 | $NO_2$ | $H_3N^\oplus-CH(CH_3)_2$ | phenyl | Cl | H | $CF_3$ | H | Cl | 64–70 (decomposition) |
| 29 | $NO_2$ | $H_3N^\oplus-CH(CH_3)_2$ | $CH_3$ | Cl | H | $SO_2CF_3$ | H | Cl | 177–180 |
| 30 | $NO_2$ | $K^\oplus$ | $CH_3$ | Cl | Cl | $CF_3$ | H | Cl | >250 |
| 31 | $NO_2$ | ½ $Mg^{2\oplus}$ | $CH_3$ | Cl | Cl | $CF_3$ | H | Cl | 147 |
| 32 | $NO_2$ | ½ $Zn^{2\oplus}$ | $CH_3$ | Cl | Cl | $CF_3$ | H | Cl | 106–117 |
| 33 | $NO_2$ | $H_3N^\oplus-CH(CH_3)_2$ | $CH_3$ | Cl | Cl | $CF_3$ | H | Cl | 105 (decomposition) |
| 34 | $NO_2$ | ½ $Mn^{2\oplus}$ | $CH_3$ | Cl | Cl | $CF_3$ | H | Cl | 114 (decomposition) |
| 35 | $NO_2$ | $Na^\oplus$ | $CH_3$ | Cl | Cl | $CF_3$ | H | Cl | >250 |

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, a clearly superior activity and also selectivity towards crop plants, compared with the prior art, is shown by the compounds of the following preparation examples (6) and (23).

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a weight of 5-15 cm are sprayed with the preparation of the active compound in such a way as to apply the particular amounts of active compound desired per unit area. The concentration of the spray liquor is so chosen that the particular amounts of active compound desired are applied to 2,000 l of water/ha. After three weeks, the degree of damage to the plants is rated in % damage in comparison to the development of the untreated control. The figures denote:

0% = no action (like untreated control)

100% = total destruction

In this test, a clearly superior activity and also selectivity towards crop plants, compared with the prior art, is shown by the compounds of the following preparation examples (6) and (23).

It will be appreciated that the instant specification and claims are set forth by way of illustration and not limitation, and that various modifications and changes may be made without department from the spirit and scope of the present invention.

We claim:

1. A 5-sulphonamido-1-aryl-pyrazole of the formula (I)

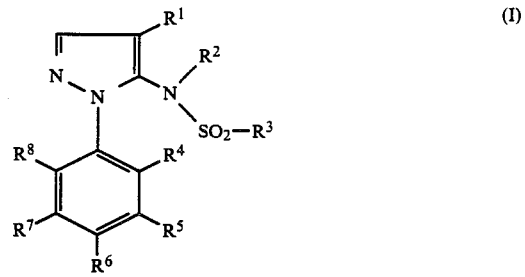

in which $R^1$ represents nitro, $R^2$ represents hydrogen, straight-chain or branched alkyl with 1 to 8 carbon atoms, a radical $R^3$—$SO_2$—, one equivalent of an alkali metal, alkaline earth metal or transition metal cation or an ammonium ion which is unsubstituted or mono-, di- or tri-substituted by identical or different substituents selected from the group consisting of methyl, ethyl, n-propyl, i-propyl, n-butyl, i-butyl, s-butyl, t-butyl and phenyl, $R^3$ represents in each case straight-chain or branched alkyl or halogenoalkyl, with in each case up to 4 carbon atoms and for said halogenoalkyl up to 9 identical or different halogen atoms, $R^4$ and $R^6$ independently of one another represent halogen or straight-chain or branched halogenoalkyl with up to 4 carbon atoms and up to 9 identical or different halogen atoms, or a radical —$S(O)_n$—$R^9$ and $R^5$, $R^7$ and $R^8$ independently of one another and independently of $R^4$ and $R^6$ represent hydrogen or halogen, wherein $R^9$ represents halogenoalkyl with up to 4 carbon atoms and with up to 9 identical or different halogen atoms, and n represents the number 2.

2. A 5-sulphonamido-1-arylpyrazole according to claim 1, wherein $R^1$ represents nitro, $R^2$ represents hydrogen, methyl, ethyl, n- or i-propyl, n-, i-, s- or t-butyl, a radical $R^3$—$SO_2$—, one equivalent of a sodium, potassium, magnesium, calcium, barium, copper, zinc, manganese, tin, iron, cobalt or nickel ion, or an ammonium ion which is unsubstituted or mono-, di- or tri-substituted by identical or different substituents selected from the group consisting of methyl, ethyl, n-propyl, i-propyl, n-butyl, i-butyl, s-butyl, t-butyl and phenyl.

$R^3$ represents methyl, ethyl, n- or i-propyl, n-, i-, s- or t-butyl, chloro-methyl, dichloromethyl, trifluoromethyl, $R^4$ and $R^6$ independently of one another represent fluorine, chlorine, bromine, iodine, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, or a radical —$S(O)_n$—$R^9$ and $R^5$, $R^7$ and $R^8$ independently of one another and independently of $R^4$ and $R^6$ represent hydrogen or halogen, wherein $R^9$ represents fluorodichloromethyl, difluoromethyl, tetrafluoroethyl, trifluorochloroethyl, trifluoromethyl, and n represents the number 2.

3. A 5-sulphonamido-1-aryl-pyrazole according to claim 1, wherein R³ is a straight-chain or branched alkyl having up to 4 carbon atoms.

4. A 5-sulphonamido-1-aryl-1-pyrazole of the formula

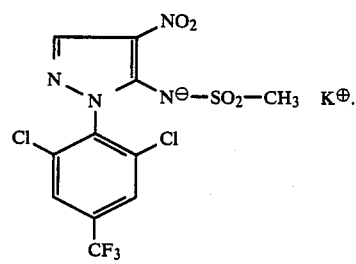

5. A 5-sulphonamido-1-aryl-pyrazole to claim 2 of the formula

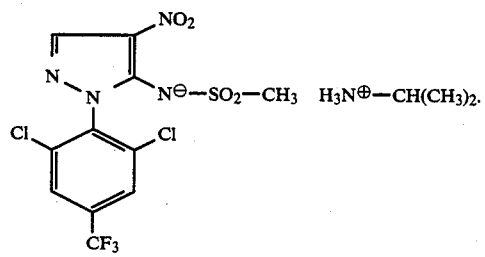

6. A 5-sulphonamido-1-aryl-pyrazole of the formula

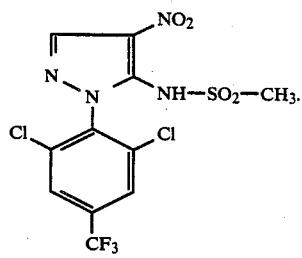

7. A 5-sulphonamido-1-aryl-pyrazole of the formula

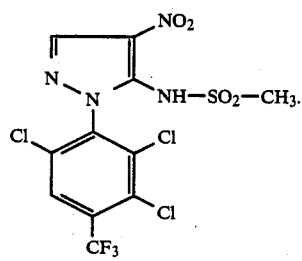

8. A 5-sulphonamido-1-aryl-pyrazole of the formula

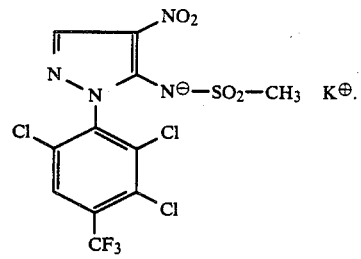

9. A 5-sulphonamido-1-aryl-pyrazole of the formula

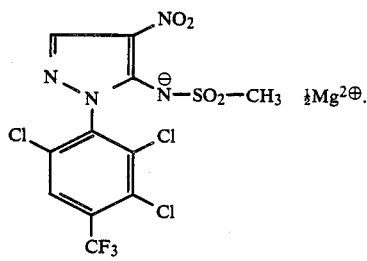

10. A 5-sulphonamido-1-aryl-pyrazole of the formula

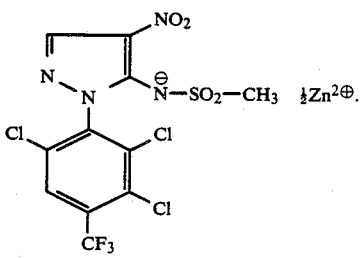

11. A 5-sulphonamido-1-aryl-pyrazole of the formula

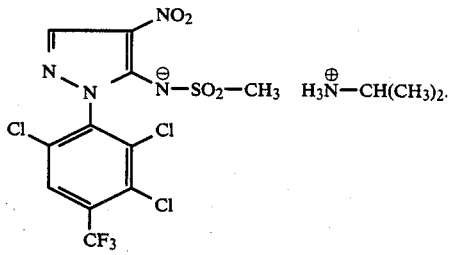

12. A method of combating weeds by applying to said weeds or a habitat thereof a herbicidally effective amount of a 5-sulphonamido-1-aryl-pyrazole of a formula selected from the group consisting of

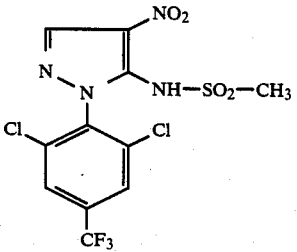

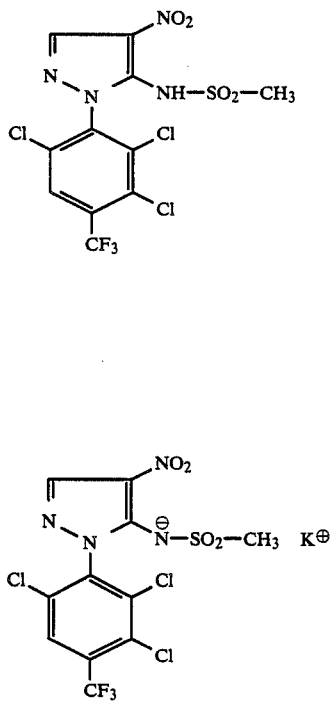

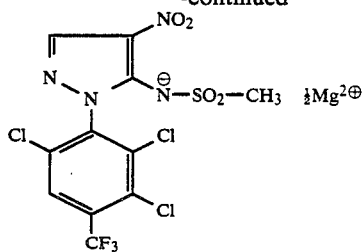

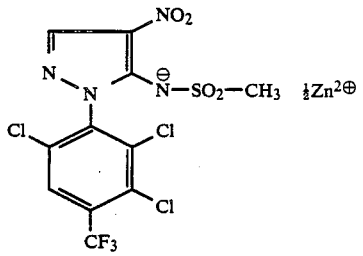

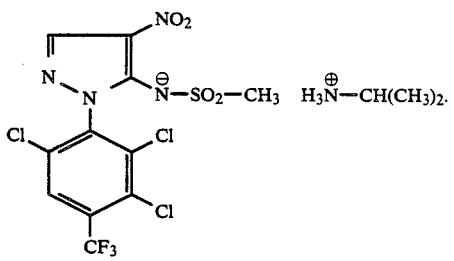

13. A herbicidal agent comprising at least one 5-sulphonamido-1aryl-pyrazole of the formula (I) according to claim 1 and an extender.

14. A herbicidal agent according to claim 13, which further comprises a surface-active agent.

15. A method of combating weeds by applying a herbicidally effective amount of a sulphonamido-1-aryl-prazoles of the formula (I) according to claim 1 on weeds and/or on the habitat thereto.

* * * * *